Figure 1:
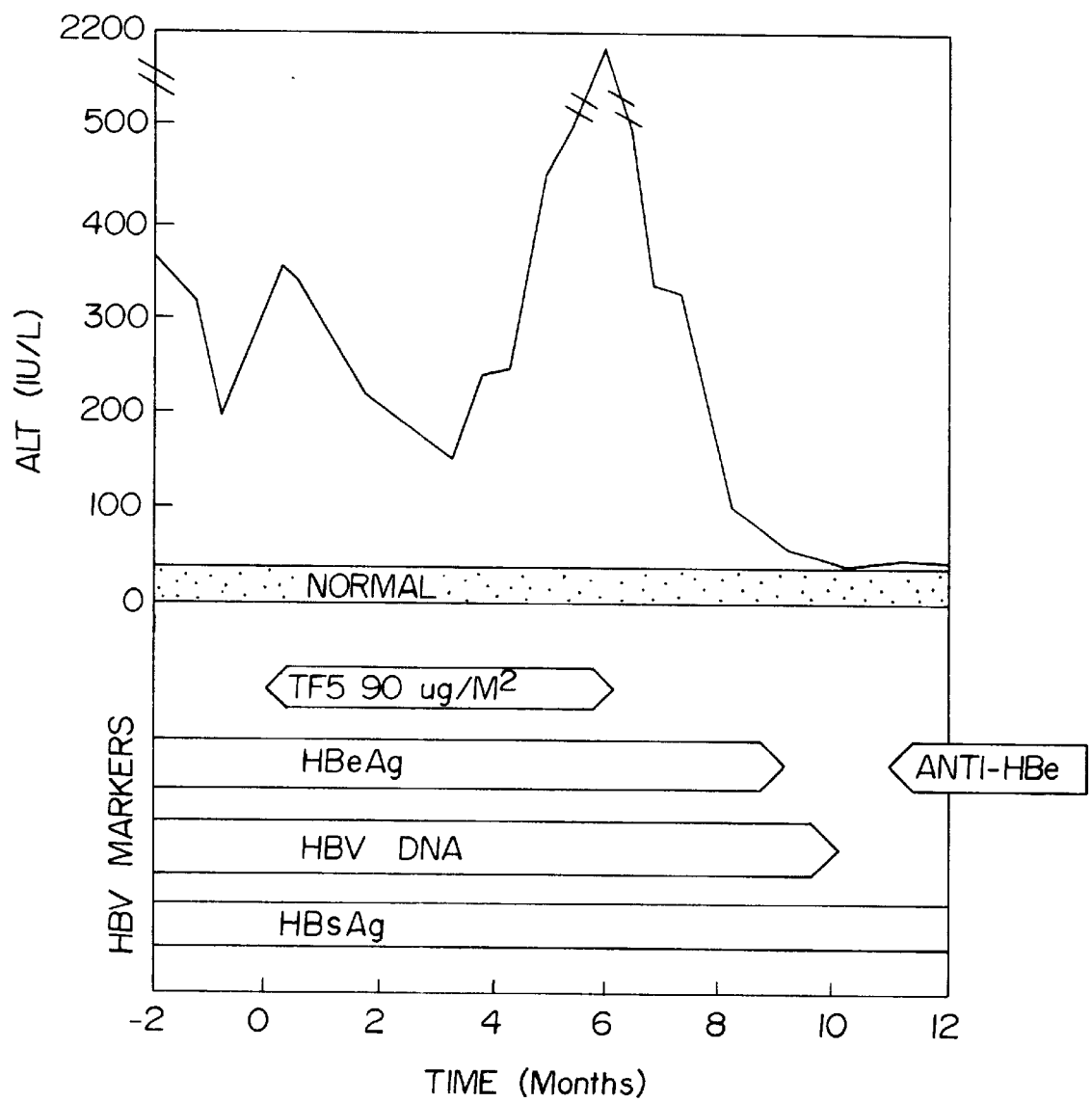

United States Patent [19]

Mutchnick

[11] Patent Number: 6,106,868

[45] Date of Patent: Aug. 22, 2000

[54] METHOD FOR THE TREATMENT OF HEPATITIS

[75] Inventor: Milton G. Mutchnick, West Bloomfield, Mich.

[73] Assignee: The Board of Governors of Wayne State University, Detroit, Mich.

[21] Appl. No.: 07/571,782

[22] Filed: Aug. 24, 1990

[51] Int. Cl.[7] .................................................. A61K 35/26
[52] U.S. Cl. .............................................................. 424/580
[58] Field of Search .............................................. 424/580

[56] References Cited

PUBLICATIONS

Eichberg et al. CA 106:117943 (1987).
Mutchnick et al. Hepatoloy 8(5)& Sep./Oct. 1988.
Eichberg et al. (Eichberg), "Effect of Thymosin Immunostimulation With and Without Corticosteroid Immunosuppression on Chimpanzee Hepatitis B Carriers," Journal of Medical Virology 21(1), pp. 25–37, 1987.
Hoofnagle et al., Hepatology 12 (4 Part 2): 846 (1990).
Kassianides et al., Journal of Medical Virology 21 (4): 122A–123A (1987).
Nevens et al., Liver 13: 15–19 (1993).
Waked et al., Journal of Chemotherapy 2(5): 310–318 (1990).
Dimopoulou et al., Gut (Supplement): S104–S105 (1993).
Perrillo et al., Gastroenterology 109: 908–916 (1995).
Seeff, L. B., et al., Sem Liver Dis 6:11–22 (1986).
Thomas, H. C., et al., Sem Liver Dis 6:34–41 (1986).
Hoofnagle, J. H., et al., Gastroenterology 95:1318–1325 (1988).
Perillo, R. P., et al., Ann Int Med 109:95–100 (1988).
Renault, P. F., et al., Sem Liver Dis 9:273–277 (1989).
Kakumu, S., et al. Hepatology, 8:487–492 (1988).
Fattovich, G., et al., Gastroenterology 91:692–696 (1986).
Romeo, F., et al., Arzheim–Forsch/Drug Res. 37:450–456 (1987).
Zhang, D–F, et al., Chinese Med. J. 99:791–798 (1986).
Dabrowski, M. P., et al., Clin. Immunol. Immunopathol. 16:297–307 (1980).
Low, T.L.K., et al., Thymus 6:27–42 (1984).
Wetzel, R., et al., Biochem 19:6096–6104 (1980).
Low, T.L.K., et al., J. Biol. Chem. 254:981–986 (1979).
Mutchnick, M. G., et al., Clin. Immunol. Immonopathol. 16:423–437 (1980).
Mutchnick, M. G., et al., Dig. Dis Sci 28: 328–334 (1983).
Marshall, G. D., et al., J. Immunol. 126:741–744 (1981).
Mutchnick, M. G., et al., Clin. Immunol. Immunopathol. 23:626–633 (1982).
Sztein, M. B., et al., Proc Natl. Acad Sci USA 83:6107–6111 (1986).
Serrate, S. A., et al. J. Immunol. 139:2338–2343 (1987).
Baxevanis, C. N., et al. Immunopharm. 13: 133–141 (1987).
Svedersky, L. P., et al., Eur. J. Immunol. 12:244–247 (1982).
Sztein, M. B., et al., Springer Semin Immunopathol. 9:1–18 (1986).
Knodell, R. G., et al., Hepatology 1:431–435 (1981).
Mutchnick, M. G., et al., Clin. Immunol. Immunopathol. 47:84–92 (1988).
Lieberman, H. M., Hepatology 3:285–291 (1983).
Zav'yalov, V. P., et al., Immunol. Lett. 22:173–181 (1989).
Davis, G. L., et al., Gastroenterology 86:1315 (1984).
Inoue, M., et al., J. Immunol. 142:4006–4011 (1989).

*Primary Examiner*—Jean C. Witz
*Attorney, Agent, or Firm*—Ian C. McLeod

[57] ABSTRACT

A method for the treatment of viral induced hepatitis B in mammals, particularly humans, by injecting a thymosin is described. The method is particularly effective in the treatment of chronic hepatitis B using bovine calf thymosin fraction 5 which contains thymosin alpha$_1$ or bovine calf or synthetic thymosin alpha$_1$.

14 Claims, 4 Drawing Sheets

METHOD FOR THE TREATMENT OF HEPATITIS

BACKGROUND OF THE INVENTION (1) Field of the Invention

The present invention relates to a method for the treatment of a mammal with viral induced hepatitis by administering a thymosin to the mammal over a period of time to produce regression of the disease. In particular, the present invention relates to the treatment of type B virus chronic hepatitis.

(2) Prior Art

Chronic type B hepatitis, a common form of chronic liver disease, is associated with increased risk for development of cirrhosis, hepatic failure and hepatocellular carcinoma (Seeff, L. B., et al., Sem Liver Dis 6:11–22 (1986)). Impaired effectiveness of the host cellular immune mechanisms in clearing hepatitis B virus (HBV) infected hepatocytes has been proposed to explain development of chronic HBV infection (Thomas, H. C., et al. Sem Liver Dis 6:34–41 (1986)). Antiviral agents have been employed in efforts to treat this disease, among which alpha-interferon (IFN-alpha) has emerged to date as the most efficacious (Hoofnagle J. H., et al., Gastroenterology 95:1318–1325 (1988); and Perillo, R. P., et al., Ann Int Med 109:95–100 (1988)). Unfortunately, IFN-alpha can cause significant side effects requiring cessation of therapy (Hoofnagle J. H., et al., Gastroenterology 95:1318–1325 (1988); Perillo, R. P., et al., Ann Int Med 109:95–100 (1988); and Renault, P. F., et al., Sem Liver Dis 9:273–277 (1989)).

Clinical trials utilizing immune modifiers in the treatment of chronic HBV, such as interleukin 2 (IL2) and levamisole have been inconclusive or have resulted in ineffective responses (Kakumu, S., et al. Hepatology, 8:487–492 (1988); Fattovich, G., et al., Gastroenterology 91:692–696 (1986)).

Thymic extracts or thymus derived peptides, which are chemically different from the thymosins, have been used in clinical trials in the treatment of chronic hepatitis B. In one study (Romeo, F., et al., Arzheim-Forsch/Drug Res. 37:450–456 (1987)), thymostimulin, an extract of calf thymus, resulted in clinical, biochemical and histological improvement; however, treatment effect on HBV markers was not reported. Similar responses have been reported in other studies using thymopeptide (Zhang, D-F, et al., Chinese Med. J. 99:791–798 (1986)) and thymic factor 'x' (Dabrowski, M. P., et al., Clin. Immunol. Immunopathol. 16:297–307 (1980)). TF5 is a partially purified extract of bovine thymus containing at least 40 peptide components, 20 of which have been purified to homogeneity or near homogeneity (Low, T. L. K., et al., Thymus 6:27–42 (1984)). Several of these peptides, including T-alpha$_1$, have been sequenced and chemically synthesized (Wetzel, R., et al., Biochem 19:6096–6104 (1980); and Low, T. L. K., et al., J. Biol. Chem. 254:981–986 (1979)).

In previous studies, thymosin fraction 5 was shown, in vitro, to decrease spontaneous cell mediated cytotoxicity in patients with CAHB (Mutchnick, M. G., et al., Clin. Immunol. Immunopathol. 16:423–437 (1980)) and to enhance Con A induced suppressor cell function in PBM from these patients (Mutchnick, M. G., et al., Dig. Dis Sci 28:328–334 (1983)).

Thymosin fraction 5 (TF5) and thymosin alpha$_1$ (T-alpha$_1$), have been shown to trigger maturational events in lymphocytes, augment T cell function and promote reconstitution of immune defects (Low, T. L. K., et al., Thymus 6:27–42 (1984)). These compositions are thus immunomodulators.

TF5 and T-alpha$_1$ are potent inducers of T cells and can influence immunoregulatory T cell function (Low, T. L. K., et al., Thymus 6:27–42 (1984); Low, T. L. K., et al., J. Biol. Chem. 254:981–986 (1979); Marshall, G. D., et al., J. Immunol, 126:741–744 (1981); and Mutchnick, M. G., et al., Clin. Immunol. Immunopathol. 23:626–633 (1982)). TF5 and T-alpha$_1$ have been shown to enhance T4 cell function, promote IFN-alpha, IFN-$\gamma$ and IL2 production by human lymphocytes, and to increase lymphocyte IL2 receptor expression (Low, T. L. K., et al., Thymus 6:27–42 (1984); Sztein, M. B, et al., Proc Natl Acad Sci USA 83:6107–6111 (1986); Serrate, S. A., et al. J. Immunol. 139:2338–2343 (1987); Baxevanis, C. N., et al., Immunopharm. 13:133–141 (1987); and Svedersky, L. P., et al., Eur. J. Immunol. 12:244–247 (1982)).

Clinical trials of TF5 and T-alpha$_1$ as primary or adjunctive therapy in patients with immunodeficiency or cancer indicate that these agents enhance immune responsiveness and augment specific lymphocyte functions (Sztein, M. B., et al., Springer Semin Immunopathol. 9:1–18 (1986)). Moreover, these thymic peptides appear to reconstitute immune defects rather than non-specifically augment relatively normal immune parameters. These compositions have not been used to treat HBV.

OBJECTS

It is therefore an object of the present invention to provide a method for producing a regression of hepatitis B in a mammal, particularly humans. Further it is an object of the present invention to provide a method which is particularly effective against chronic hepatitis B. These and other objects will become increasingly apparent by reference to the following description.

IN THE DRAWINGS

FIG. 1 shows the response to TF5 (90 mg/M$^2$) in a single patient who first cleared serum HB$_e$Ag followed by HBV DNA after demonstrating a flare in ALT values. Anti-HB$_e$ developed shortly thereafter, however, serum HB$_s$Ag persisted. HBV DNA molecular forms and HB$_c$Ag present in the initial and 6 month liver biopsy specimens were not seen in the 12 month biopsy specimen.

Figure 2A:
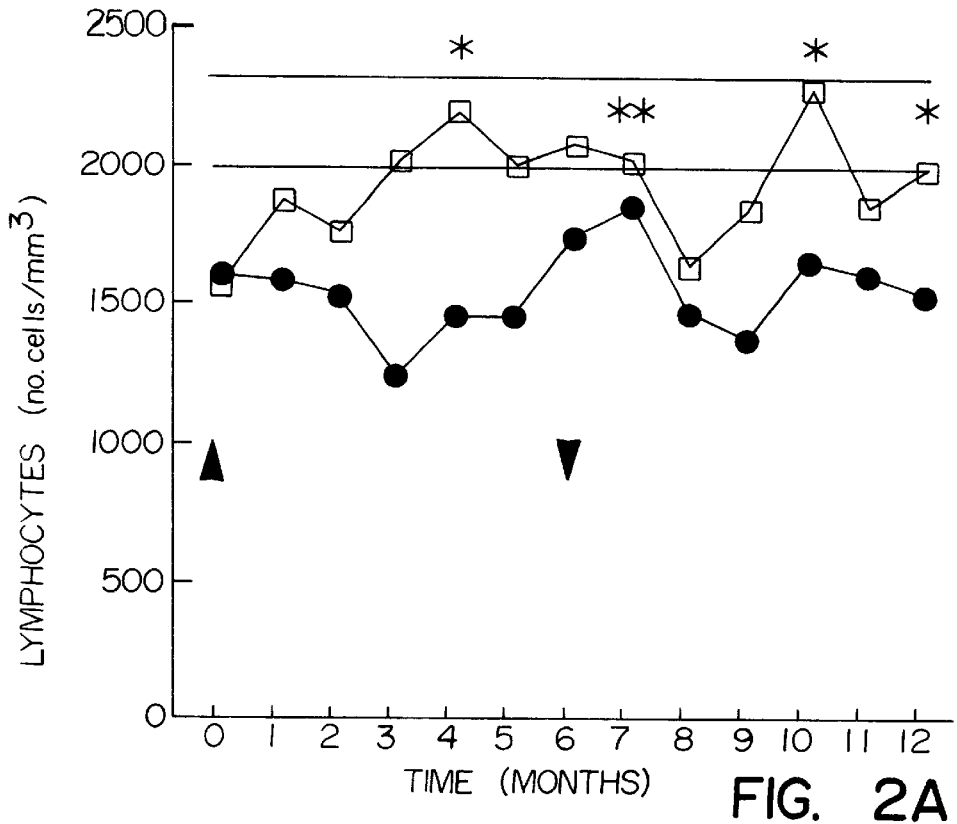
Figure 2B:
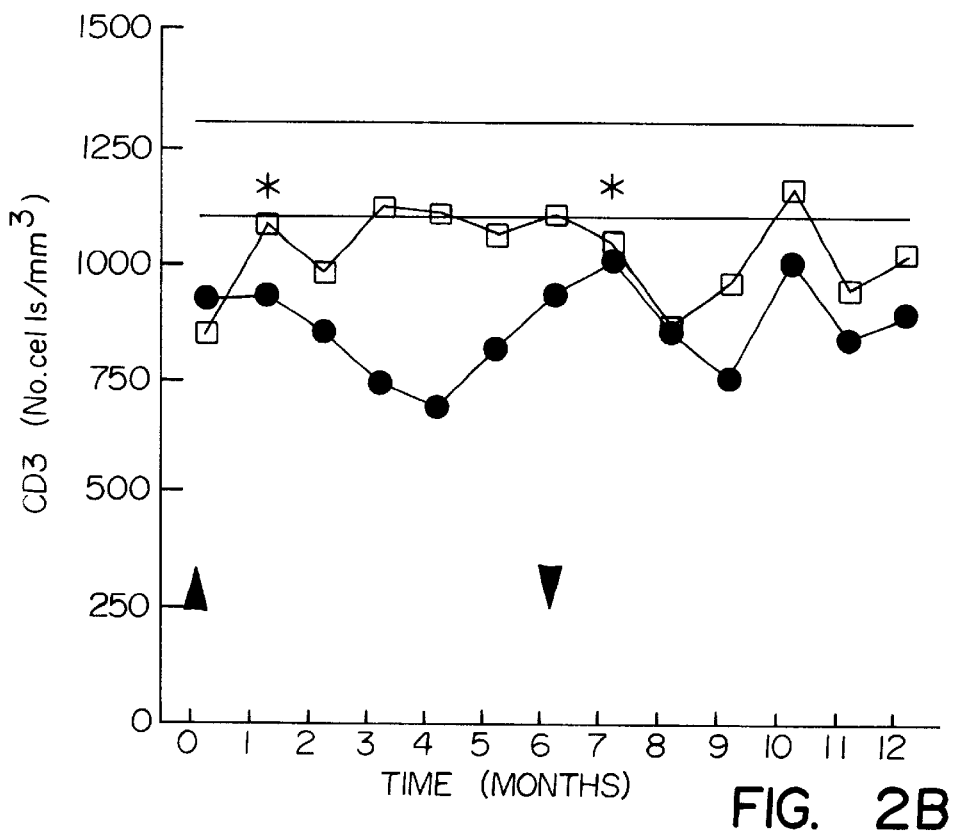
Figure 2C:
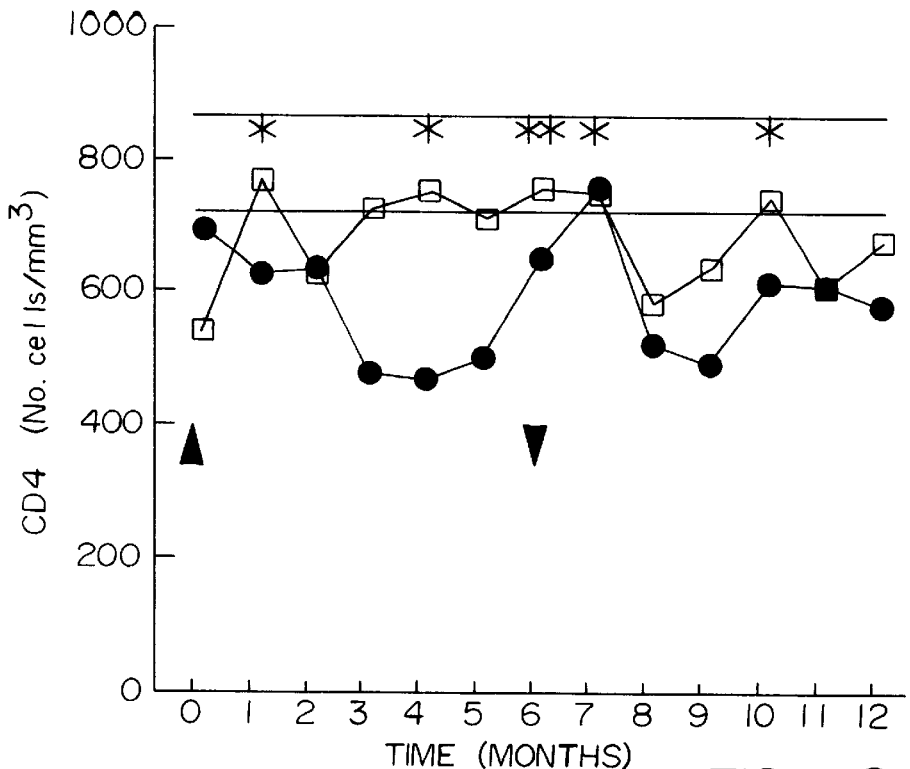

FIG. 2 shows serial analyses of peripheral blood absolute (A) lymphocyte (B) CD3 and (C) CD4 counts in the patient groups. Comparisons were made between the □, TF5/T-alpha$_1$ group and ●, placebo group as well as to a panel (n=67) of healthy volunteers with a 95% confidence limit as shown between parallel lines. *p<0.05, **p<0.01 when each value was compared to inclusion value by Student's paired t test. ▲, time at which treatment was initiated; ▼, treatment completed.

Figure 3:
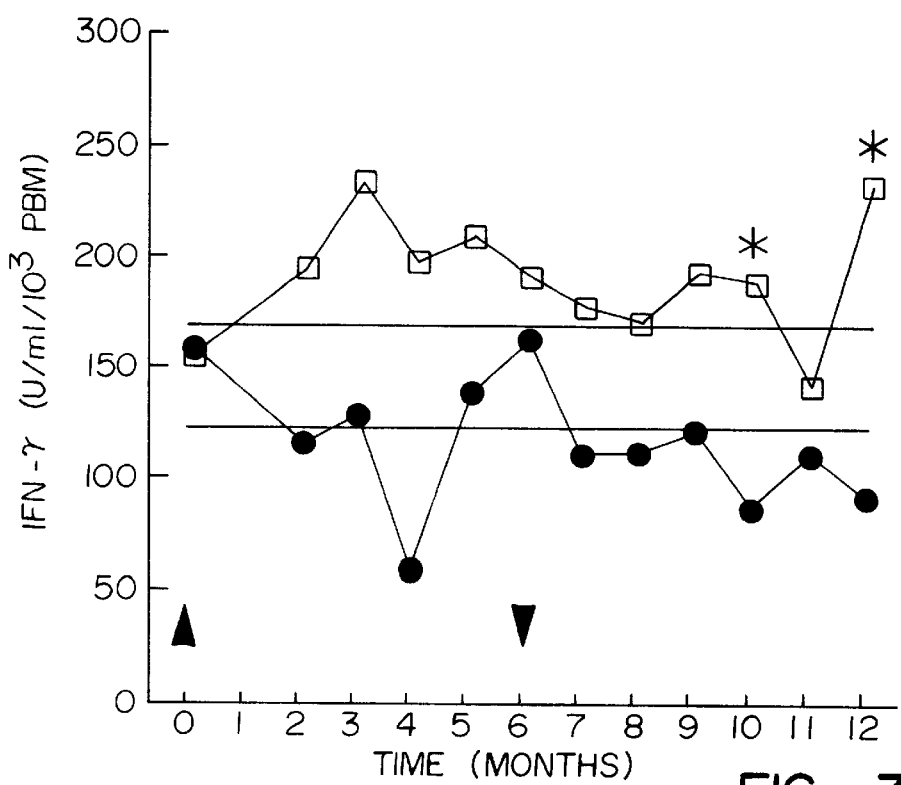

FIG. 3 shows serial analysis of IFN-$\gamma$ production by PBM obtained from □, TF5/Talpha$_1$ group and ●, placebo group. Comparisons were made between the patient groups and to healthy volunteers (n=67) with a 95% confidence limit as demarcated by the parallel lines. *p<0.05, when value was compared to inclusion value, Student's paired t test. ▲, time at which treatment was initiated; ▼, treatment completed.

Figure 4:
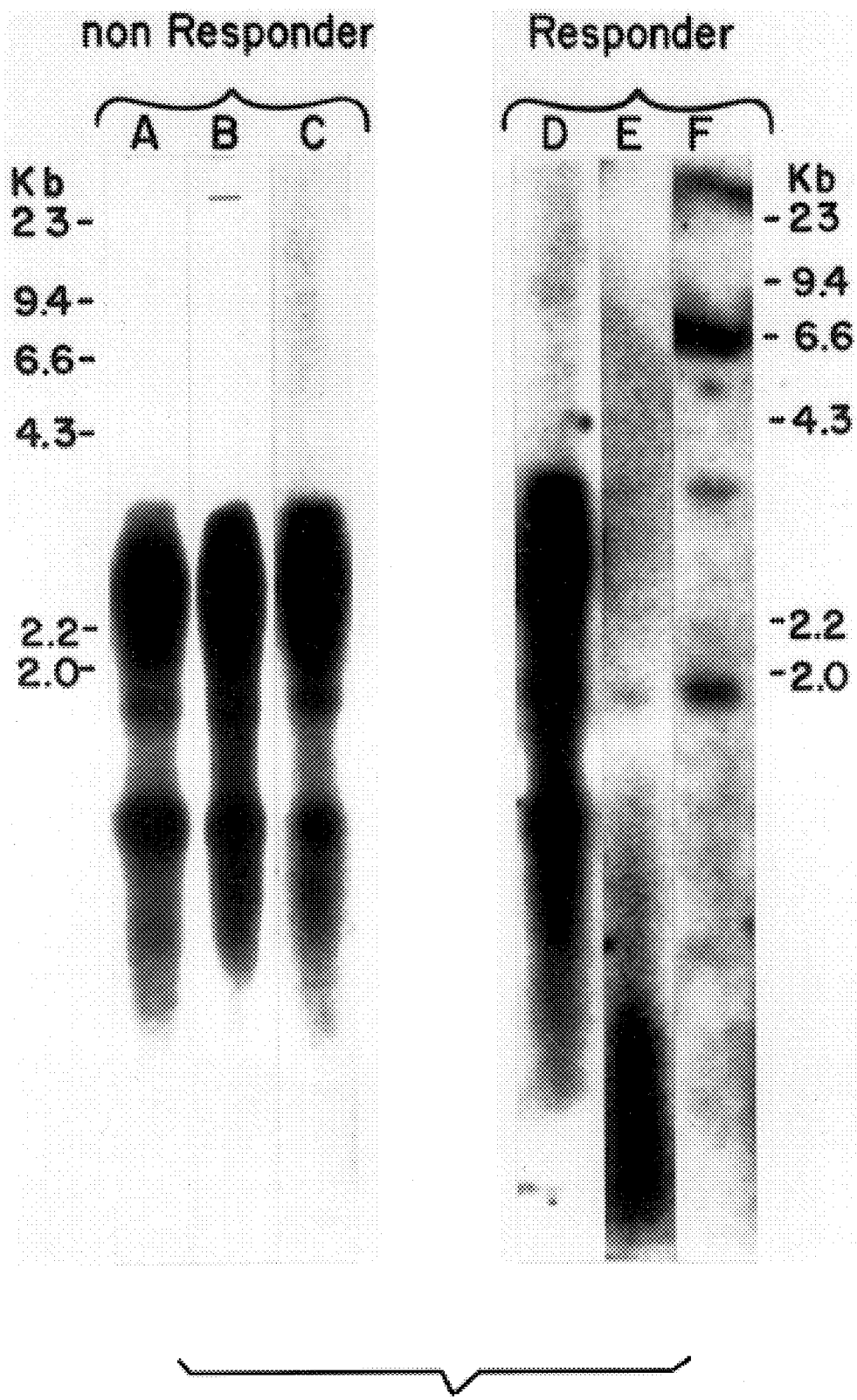

FIG. 4 shows the results of HBV DNA hybridization studies of liver biopsy specimens in a non-responder given placebo and in a responder treated with thymosin. Southern blot analysis reveals that in lanes A, B and C from the patient treated with placebo, all of the expected forms of HBV DNA replicative intermediates are present in high amounts and are unchanged over the 12 month study period (A, inclusion; B, 6 months; C, 12 months). Similar replicative forms were present at inclusion (lane D) in the patient given T-alpha$_1$, but only supercoiled and relaxed circular free genomes were present at 6 months (lane E) and at 12 months (lane F).

GENERAL DESCRIPTION

The present invention relates to a method for the treatment of a viral induced hepatitis in a mammal which comprises: administering an effective dosage of a thymosin selected from the group consisting of thymosin alpha$_1$ and a bovine calf extract containing thymosin alpha$_1$ in an effective amount to the mammal, thereby producing a regression of the hepatitis in the mammal. The method is particularly effective against chronic hepatitis B in humans.

The preferred thymosins are thymosin alpha$_1$ and thymosin fraction 5 which is a mixture of thymosins including an effective amount of thymosin alpha$_1$. Thymosin fraction 5 is derived from bovine thymus and thymosin alpha$_1$ can be synthesized chemically as shown in the references previously cited.

The thymosin is preferably administered subcutaneously in a diluent, such as sodium bicarbonate. Such diluents are well known to those skilled in the art.

The dosage in humans is used in an amount preferably between about 600 and 1200, most preferably 900 micrograms, per square meter of body area for thymosin alpha$_1$ in humans. Thymosin fraction 5 is used in an amount preferably between about 60 and 120, most preferably 90 milligrams, per square meter of body area in humans. The dosage is selected for optimal results in terms of regression of the virus. In animals, the dosages are comparable.

SPECIFIC DESCRIPTION

The safety and efficacy of thymosin fraction 5 and thymosin alpha$_1$ in a prospective, randomized, double-blind and placebo-controlled trial in 12 patients was assessed with chronic active hepatitis B. All patients had histologic and biochemical evidence of active liver disease for at least 6 months prior to treatment and were positive for serum hepatitis B virus deoxyribonucleic acid and hepatitis B surface antigen. Seven patients received thymosin fraction 5 or thymosin alpha$_1$ and 5 patients received placebo subcutaneously, twice weekly for six months. At the conclusion of the study (1 yr), serum amino transferase levels improved significantly in thymosin treated patients, but not in the placebo group. Six (86%) of the thymosin treated patients and 1 (20%) patient given placebo cleared hepatitis B virus deoxyribonucleic acid from the serum (p<0.04, Fisher's exact test). After treatment, replicative forms of hepatitis B virus deoxyribonucleic acid were present in liver specimens from 4 of 5 placebo treated patients but in only 1 of 7 thymosin treated patients (p<0.04, Fisher's exact test). Response to thymosin therapy was associated with significant improvements in peripheral blood lymphocyte, CD3 and CD4 counts and in in vitro production of interferon gamma over initial values. No significant side effects were observed in patients given thymosin. Clinical, biochemical and serological improvements in patients responding to thymosin were sustained at 26±3 months of follow up. The results show that thymosin therapy promotes disease remission and cessation of hepatitis B virus replication in patients with hepatitis B virus chronic active hepatitis.

METHODS

PATIENTS

Patients between the ages of 18 and 70 years with chronic type B hepatitis were included based on the following criteria: Presence of hepatitis B surface antigen (HB$_s$Ag) and elevated serum alanine aminotransferase (ALT) levels for at least 6 months; positive serum test for hepatitis B virus DNA (HBV DNA); histologic confirmation of CAH (Knodell, R. G., et al., Hepatology, 1:431–435 (1981)) within the previous 3 months of randomization and evidence of compensated liver disease (prolongation of prothrombin time less than 4 seconds over control values, serum albumin$\geq$3 gm/dl, and serum total bilirubin$\geq$4 mg/dl). Additional requirements included a hemoglobin$\geq$10 gm, a platelet count$\geq$70,000/mm$^3$, a white cell count (WBC)$\geq$3000/mm$^3$, a polymorphonuclear count (PMN)$\geq$1500/mm$^3$ and serum creatinine$\leq$1.4 mg/dl. Patients with a history of hepatic encephalopathy, bleeding esophageal or gastric varices, previous antiviral or immunosuppressive therapy were excluded. Additional causes for ineligibility included a history of intravenous drug abuse, presence of hepatitis D antibody, malignancy, pregnancy, homosexuality and a positive test for antibody to human immunodeficiency virus. Women agreed to practice birth control for the duration of the study (1 year) and to avoid use of contraceptive medications.

STUDY PROTOCOL

In this 3 arm study, patients were randomly assigned by a computer generated program to receive TF5 (90 mg/M$^2$ body surface area), T-alpha$_1$ (900 μg/M$^2$ body surface area) or placebo by subcutaneous (SC) injection twice weekly for 6 months. TF5, synthetic T-alpha$_1$ and placebo (1.4% sodium bicarbonate) were supplied by Alpha One Biomedicals, Inc., Foster City, Calif. Patients were instructed on self administration of SC injections and compliance was monitored weekly by nurse clinicians. Patients were seen at 2 week intervals for 6 months and then monthly for an additional 6 months. Clinical and laboratory assessments were obtained at each visit and included serum analysis for HB$_s$Ag, antibody to HB$_s$Ag (anti-HB$_s$), hepatitis B e antigen and antibody (HB$_e$Ag and anti-HB$_e$, respectively), HBV DNA, ALT, aspartate aminotransferase (AST), total bilirubin, alkaline phosphatase, blood urea nitrogen (BUN), creatinine, cholesterol, uric acid and total protein. Monthly determinations of serum albumin, hemoglobin, WBC, PMN, lymphocytes and platelet counts were obtained. Prothrombin time was monitored monthly, as was routine urine analysis. Immunological analyses were conducted prior to treatment and monthly thereafter for the study period (1 year). Analysis of peripheral blood lymphocytes included absolute numbers for CD3, CD4, CD8, CD11 and NK subsets by indirect immunofluorescence staining using a modification of a previously described method (Mutchnick, M. G., et al., Clin. Immunol. Immunopathol. 47:84–92 (1988)), concanavalin A (Con A) and phytohemagglutinin-P (PHA-P) induced lymphocyte transformation, and peripheral blood mononuclear cell (PBM) production of IFN-γ using solid-phase radioimmunoassay (IMRX Interferon-y RIA, Centocor Inc., Malvern, Pa.; (Mutchnick, M. G., et al., Clin. Immunol. Immunopathol. 47:84–92 (1988)). Blood samples obtained from healthy adult volunteers were included for each of the above assays and constituted a panel of normal values used in statistical analyses. Percutaneous liver biopsy was repeated in most patients at 6 months and in all patients at 1 year. A positive response to treatment was defined as loss of serum HBV DNA, $HB_eAg$ (if present initially), and normalization or near normalization of ALT and AST levels at 1 year.

The protocol was approved by the Human Investigation Committee of Wayne State University School of Medicine and fully informed, written consent obtained from all patients.

Viral Markers

Serum $HB_sAg$ and anti-$HB_s$ were determined by radioimmunoassay (RIA) and both $HB_eAg$ and anti-$HB_e$ antibody by enzyme-linked immunosorbent assay (ELISA). Antibody to the Delta virus was tested by RIA and antibody to the hepatitis C virus by ELISA.

Histologic Assessment of Liver Biopsy Specimens

All liver biopsy specimens stained with hematoxylin-eosin and trichrome were analyzed under code by a single observer according to a system devised for asymptomatic chronic active hepatitis (Knodell, R. G., et al., Hepatology, 1:431–435 (1981)). This system evaluated independently the four features of periportal and bridging necrosis; intralobular damage, including necrosis; portal inflammation; and fibrosis, including cirrhosis. Each feature was given a score, resulting in a histologic activity index that is the total of all the scores. Specimens were also stained for hepatitis B core antigen ($HB_cAg$), using the peroxidase antiperoxidase techniques (PAP). When possible, portions of liver biopsy tissue were snap frozen in liquid nitrogen and analyzed by hybridization for the presence of HBV DNA molecular forms.

HBV Hybridization Studies

Serum was analyzed for the presence of HBV DNA sequences by spot hybridization as previously reported (Lieberman, H. M., Hepatology 3:285–291 (1983)), except that the proteinase K digestion step was not included. This increased the sensitivity of the assay by a factor of 10, with little increase in background radioactivity with negative control serum. This assay detected as little as 0.05–0.10 pg of purified HBV DNA applied as a simple spot in a 5 $\mu$l aliquot. Sera that were negative by direct spot hybridization were confirmed as negative by extracting total nucleic acid from a 200 $\mu$l aliquot and applying the total extract as a single spot (Lieberman, H. M., Hepatology 3:285–291 (1983)). For these studies, it was critical to use a highly purified HBV DNA probe which did not produce a positive hybridization signal with 0.1 $\mu$g of control plasmid DNA (pBR322) applied to the filter.

Liver biopsy tissues were homogenized in a Dounce homogenizer in 50 mM Tris-HCl, pH 7.5–150 mM NaCl-25 mM EDTA and DNA was isolated by SDS-proteinase K digestion, phenol-chloroform extraction and ethanol precipitation. Purified HBV DNA (3200 bp) was labelled with [$^{32}$P] to high specific activity (2–8×10$^8$ con. g DNA) by random primer extension. Ten micrograms of DNA were electrophoresed through 0.8% agarose gels either undigested or after digestion with restriction endonuclease Hind III or EcoR1. The DNA was transferred to a GeneScreen filter and fixed to the filter by UV irradiation for 1 minute. Positive and negative control samples were included in each experiment.

Prehybridization was performed in 5×SSC–0.1% SDS—50% formamide—5×Denhardt's solution—200 $\mu$g/ml denatured salmon sperm DNA at 42° C. overnight. Hybridization was performed under similar conditions with the addition of [$^{32}$P] labelled probe for 48 hours. Filters were washed in 2×SSC–0.1% SDS at room temperature twice for 5 minutes each; 1×SSC–1% SDS at 65° C. twice for 30 minutes each; and 0.1×SSC–0.1% SDS at room temperature for 15 minutes. They were then exposed to Kodak XAR-5 film at −70° C. using two intensifying screens.

Statistics

Group means were compared by Student's 2-tailed t test. Changes in the measurements between the inclusion values and subsequent time points were compared by Student's 2-tailed paired t test.

RESULTS

In this pilot study, twelve patients were assessed; four patients were randomized to receive TF5, three to receive T-alpha$_1$ and five to receive placebo. Two patients given TF5 experienced local discomfort at the injection site and were changed to T-alpha$_1$ within 1 month. The final study groups consisted of 7 patients receiving TF5 or T-alpha$_1$ (thymosin group) and 5 patients given placebo. At inclusion, the thymosin and placebo groups were comparable with respect to sex, age, biochemical and serological parameters (Table 1). None of the patients tested positive for delta antibody and only one patient, who responded to T-alpha$_1$ treatment, was positive for antibody to Hepatitis C.

TABLE 1

Characteristics of Study Groups at Inclusion

| Characteristic | Treated Group (TF5/Talpha$_1$) | Control Group Placebo |
|---|---|---|
| Number | 7 | 5 |
| Male:Female | 5:2 | 3:2 |
| Age (yr) | 47(26–67)* | 48(23–64) |
| Duration of HB$_s$Ag (mo) | 31(7–90) | 24(7–60) |
| ALT (IU/L)** | 196(33–475) | 116(67–179) |
| AST (IU/L) | 160(51–490) | 176(113–295) |
| Bilirubin (mg/dl) | 0.7(0.5–1.1) | 1.3(0.5–3.4) |
| Albumin (g/dl) | 4.1(3.1–4.7) | 3.5(2.9–4.1) |
| Prothrombin time (sec) | 13.1(12.3–14.2) | 12.9(12.0–14.3) |
| HBV DNA (0–5+) | 2.1(0.5–3.0+) | 1.6(0.5–2.5+) |

*Geometric mean (range)
**Normal values: ALT < 40 IU/L, AST < 45 IU/L, bilirubin < 1.5 mg/dl, albumin 3.5–5.2 g/dl.

Clearance rates for HBV DNA, $HB_eAg$ and $HB_sAg$ at completion of the trial (12 months) are shown in Table 2 and indicate a significantly higher HBV DNA clearance rate in the thymosin group as compared to the placebo group (86% versus 20%, respectively, p<0.04, Fisher's exact test). Serum HBV DNA levels decreased in all 6 patients responding to thymosin during the 6 month treatment period. Serum HBV DNA disappeared in 4 patients during treatment and in the remaining 2 patients at 2 and 6 months, respectively, after completing treatment.

TABLE 2

HBV Marker Seropositivity at Inclusion and at 12 Months

| Study Group | HBV DNA | | Hb$_s$Ag | | HB$_e$Ag | |
|---|---|---|---|---|---|---|
| | Inclusion n (%) | 12 Mos. n (%) | Inclusion n (%) | 12 Mos. n (%) | Inclusion n (%) | 12 Mos. n (%) |
| Treated (TF5/Talpha$_1$) | 7 (100) | 1 (14)* | 7 (100) | 6 (86) | 6 (86) | 1 (14) |
| Controls | 5 (100) | 4 (80) | 5 (100) | 5 (100) | 3 (60) | 3 (60) |

*p < 0.04 when compared to placebo group, Fisher's exact test

Patients treated with TF5 or Talpha$_1$ showed normal or near normal ALT and AST values at 1 year which were significantly lower than corresponding values in patients treated with placebo (Table 3). However, transient ALT elevations (2–6 fold over pre-inclusion values) were observed in 5 of the 6 responders to thymosin. The duration of these ALT flares was 4.6±0.6 weeks, n=5, and preceded clearance of HBV DNA in each case (FIG. 1).

TABLE 3

Aminotransferase Levels During Study Period

|  | Treated (7)* | Controls (5) | P |
|---|---|---|---|
| ALT (IU/l) |  |  |  |
| Inclusion | 196 ± 62** | 116 ± 18 |  |
| 6 Months | 88 ± 50 | 97 ± 22 |  |
| 12 Months | 42 ± 5 | 169 ± 68 | <0.05 |
| 27 ± 3 Months | 29 ± 5 | — |  |
| 26 ± 3 Months *** | 26 ± 5 | — |  |
| AST (IU/l) |  |  |  |
| Inclusion | 160 ± 57 | 176 ± 35 |  |
| 6 Months | 53 ± 12 | 121 ± 26 | <0.05 |
| 12 Months | 43 ± 7 | 171 ± 53 | <0.02 |
| 27 ± 3 Months | 38 ± 10 | — |  |
| 26 ± 3 Months *** | 29 ± 4 | — |  |

*( ), Number of Patients.
**Means ± SEM.
*** Value for 6 responders only.

Long term follow up of the thymosin group (27±3 months) revealed persistently negative serum HBV DNA in the 6 responders and normalization of ALT levels in all 7 patients (29±5 IU/L). By 14 months of follow up, 2 thymosin responders (29%) had cleared serum HB$_s$Ag and formed anti-HB$_s$.

Prior to randomization, the 12 patients had significantly decreased peripheral blood lymphocyte (p<0.01), CD3 (p<0.02), CD4 (p<0.05) and CD11 (p<0.05) counts when compared to healthy volunteers (n=67). No differences were noted in CD8 and NK counts or in CD4/CD8 ratios between CAHB patients and healthy volunteers. No significant differences were observed in lymphocyte, T cell subset or NK counts between the thymosin and placebo groups at inclusion, although the lymphocyte, CD3 and CD4 counts were significantly lower in the treated group when compared to healthy volunteers (Table 4).

TABLE 4

Absolute Lymphocyte and T Cell Subset Counts in Peripheral Blood (No. cells/mm3; Means ± SEM)

|  | Inclusion | | 6 Months | |
|---|---|---|---|---|
| TEST | Treated(7)* | Controls(5) | Treated(7) | Controls(5) |
| Lymphocytes | 1568 ± 190** | 1603 ± 175 | 2082 ± 227 | 1745 ± 200 |
| CD11 | 976 ± 114 | 972 ± 134 | 1109 ± 122 | 952 ± |
| CD3 | 848 ± 104** | 923 ± 113 | 1107 ± 128 | 932 ± 112 |
| CD4 | 541 ± 86** | 695 ± 140 | 761 ± 102 | 651 ± |
| CD8 | 353 ± 62 | 271 ± 45 | 387 ± 44 | 349 ± 61 |
| CD4/CD8 | 1.7 ± | 2.1 ± 0.4 | 2.0 ± 0.1 | 1.0 ± 0.2 |
| NK | 102 ± 20 | 66 ± 15 | 63 ± 13 | 58 ± 20 |

TABLE 4-continued

Absolute Lymphocyte and T Cell Subset Counts in Peripheral Blood (No. cells/mm3; Means ± SEM)

|  | 12 Months | | Healthy Volunteers |
|---|---|---|---|
| TEST | Treated(7) | Controls(5) | (67) |
| Lymphocytes | 1994 ± 88 | 1532 ± 350 | 2154 ± 84 |
| CD11 | 1012 ± 34*** | 854 ± 206 | 1253 ± 53 |
| CD3 | 1019 ± 42** | 885 ± 220 | 1200 ± 52 |
| CD4 | 679 ± 45 | 579 ± 169 | 796 ± 37 |
| CD8 | 344 ± 31 | 307 ± 58 | 404 ± 20 |
| CD4/CD8 | 2.1 ± 0.2 | 1.9 ± 0.2 | 2.1 ± 0.1 |
| NK | 49 ± | 40 ± | 72 ± |

*( ), Number of Subjects
**p < 0.05, Compared to healthy volunteers
***p < 0.001, Compared to healthy volunteers FIG. 2 illustrates that within 1 month of initiating treatment, the thymosin group exhibited generally higher lymphocyte, CD3 and CD4 counts when compared to initial values than did the placebo group. These increases were generally sustained during the 6 month follow up period. No significant changes were noted in these parameters in the placebo group. At inclusion, no differences were found in in vitro IFN-γ production or in Con A and PHA-P lymphocyte proliferation assays between the study groups or between either study group and healthy volunteers (FIG. 3). After inclusion, PBM synthesis of IFN-γ in the thymosin group rose to levels above those seen with the healthy volunteers, whereas values in the placebo group were generally lower (FIG. 3).

Results of liver biopsy histologic activity scores are presented in Table 5.

TABLE 5

Histologic Grading of Liver Biopsy Specimens

|  | (Mean score ± SD) Study Group | | |
|---|---|---|---|
|  | Treated (7) | Controls (5) | P* |
| Inclusion Specimen |  |  |  |
| Total score | 11.1 ± 2.0 | 9.8 ± 1.3 | NS |
| Excluding collagen** | 7.1 ± 2.0 | 5.8 ± 1.3 | NS |
| Final Specimen (12 mos) |  |  |  |
| Total score | 8.4 ± 1.3 | 11.6 ± 1.7 | <0.01 |
| Excluding collagen | 4.6 ± 1.3 | 7.8 ± 1.9 | <0.02 |

*P values, Student's t test; NS, not significant.
**Histologic activity score excluding the score for fibrosis.

During the 12 month study period, histologic activity scores in 6 of the 7 thymosin treated patients decreased, while rising slightly in the seventh patient. The histologic score increased in 4 placebo patients and decreased in the fifth. All 12 CAHB patients had cirrhosis at the time of the initial biopsy and since cirrhosis was still demonstrable in the last biopsy in 6 of the 7 thymosin treated and in 4 of the 5 placebo treated patients, the changes in score were due almost entirely to changes in inflammatory activity and lobular damage. These results were significant at the p<0.01 level (Table 5). At 12 months, HB$_c$Ag was not detected by PAP staining in liver biopsy specimens from the 6 responders to thymosin and in the 1 patient given placebo, who experienced spontaneous remission. However, HB$_c$Ag was identified in the single non-responder to thymosin treatment and in the 4 remaining placebo patients.

HBV DNA molecular forms in liver were examined in 3 thymosin treated patients from whom pretreatment, 6 month and 12 month tissue specimens were available. One patient (the single non-responder to thymosin treatment) had replicative forms of HBV DNA in all three samples. In the remaining 2 patients, treatment with thymosin was associated with elimination of HBV replicative forms seen in the initial specimens. In one of these patients, no HBV DNA molecular forms were identified in the final specimen, whereas in the other, supercoiled and relaxed circular genomes remained in the final 12 month specimen (FIG. 4, responder). Two other patients who responded to thymosin showed supercoiled HBV DNA, but no replicative forms in the 6 and 12 month specimens, respectively. In 2 patients in whom pretreatment frozen liver was not available, cessation of HBV DNA replication during thymosin treatment was demonstrated by in situ hybridization of paraffin embedded tissues used for histologic studies. Therefore, objective evidence for cessation of HBV replication in liver tissue by either Southern blot or in situ hybridization analysis was obtained in all patients who responded serologically and histopathologically to thymosin treatment. Four of 5 placebo patients had replicative forms of HBV DNA in both the pretreatment and 12 month biopsy specimens (FIG. 4, non-responder). The remaining placebo patient (spontaneous remission) was negative by Southern blot for HBV DNA molecular forms in the 12 month specimen.

Therapy with TF5 and T-alpha$_1$ was not associated with significant side effects. Three patients reported local discomfort at the sites of the TF5 injections during the first 2 weeks. Two of these patients were changed to T-alpha$_1$ without further difficulty and the third patient insisted on continuing TF5. In the latter, local discomfort gradually disappeared without subsequent complication. No local, systemic or constitutional symptoms were observed with T-alpha$_1$ administration. No alterations were observed in hematologic status, biochemical parameters or in renal function, including creatinine clearance, throughout the treatment and follow up periods (data not shown). Seven patients (5 treated, 2 placebo) complained of mild to moderate fatigue prior to randomization. At the conclusion of the 12 month study, 1 treated patient (non-responder) and 1 placebo patient still experienced fatigue.

TF5 and T-alpha$_1$ are not believed to possess antiviral properties ((Zav'yalov, V. P., et al., Immunol. Lett. 22:173–181 (1989)). The results of the present trial suggest that the salutory responses to these agents are derived from immunomodulatory effects of these peptides. The significant increases in lymphocyte, CD3 and CD4 counts observed in the thymosin treated patients parallel the in vitro effects of thymosin as reported previously (Baxevanis, C. N., et al., Immunopharm 13:133–141 (1987)). IFN-γ production by PBM from patients with CAHB at entry into the study did not differ from healthy control values, as reported previously (Davis, G. L., et al., Gastroenterology 86:1315 (1984); and Inoue, M., et al., J. Immunol. 142:4006–4011 (1989)). Therefore, enhanced production of IFN-γ by PBM from thymosin but not placebo treated patients, observed during the 12 month study (FIG. 3), may represent an in vivo thymosin effect on immunoregulatory function (Mutchnick, M. G., et al., Clin. Immunol. Immunopathol; 23:626–633 (1982); Serrate, S. A., J. Immunol.; 139:2338–2343 (1987); and Baxevanis, C. N., et al. Immunopharm.; 13:133–141 (1987)) or perhaps modulation of T lymphocyte IL2 production resulting in up regulation of IFN-γ production (Svedersky, L. P., et al., Eur. J. Immunol.; 12:244–247 (1982)).

Although the mechanism(s) by which thymosins mediate their effects is unknown, there is evidence to suggest that T-alpha$_1$ may function in a manner similar to IFN-alpha. The C-terminal sequence of IFN-alpha shares homology (36%) with prothymosin alpha, the precursor form of T-alpha$_1$ (Zav'yalov, V. P., et al., Immunol. Lett., 22:173–181 (1989)). Unlike the N-terminal domain of IFN-alpha, which may direct antiviral activity, the C-terminal domain may be responsible for IFN-alpha immunomodulatory activity. Furthermore, the octapeptide corresponding to the region of highest homology between IFN-alpha$_2$ and T-alpha$_1$ compete for the same receptors on thymocytes responsible for induction of proliferation in the presence of Con A ((Zav'yalov, V. P., et al., Immunol. Lett.; 22:173–181 (1989)).

For the most part, resolution of disease and loss of HBV replication occurred gradually. None of the six patients who responded to thymosin have redeveloped serum HBV DNA (26±3 months) and all have normal ALT values (26±5 IU/l). Histologic improvement in the 12 month liver biopsy specimens of treated patients suggests decreased inflammation, hepatocyte damage and necrosis (Table 5). Hybridization studies showed either no HBV DNA molecular forms or residual free genomes, but not replicative forms, in the final liver biopsy specimens (12 months) of responders to thymosin therapy. In placebo treated patients, however, replicative HBV DNA remained present in the liver tissue, except for the one patient with spontaneous remission. The patient illustrated in FIG. 4 who responded to T-alpha$_1$ (lanes D, E and F) became serum HB$_s$Ag and HBV DNA negative during the 6 month period of T-alpha$_1$ treatment and remained negative for the 6 months following therapy at which time anti-HB$_s$ developed. This suggests that although HBV DNA remained present in the liver tissue in free genome form, the HBV infection had become latent, as there was neither viral protein production (HB$_s$Ag) nor active virus replication (HBV DNA).

The patients in this study were relatively homogeneous in that none were known to be homosexual, intravenous drug abusers or HIV positive. All had histologic evidence of active cirrhosis. The results show that TF5 and T-alpha$_1$ are non-toxic in the dosages utilized and promote resolution of disease activity in patients with CAHB. Furthermore, improvements in clinical, immunologic and histologic parameters are associated with cessation of HBV replication and either elimination of HBV DNA from liver tissue or conversion from replicative forms to free genomes with transition to a latent form of infection.

It is intended that the foregoing description be only illustrative of the present invention and that the present invention be limited only by the hereinafter appended claims.

I claim:

1. A method for the treatment of a viral hepatitis patient having hepatic decompensation as defined as cirrhosis of the liver that results in hepatic failure which comprises:
   administering by injection subcutaneously an effective dosage of a thymosin selected from the group consisting of thymosin alpha 1 and a bovine calf extract containing thymosin alpha 1 in an effective amount so as to render said patient seronegative for the hepatitis viral DNA.

2. The method of claim 1 wherein the viral hepatitis is hepatitis B virus.

3. The method of claim 1 wherein the thymosin is thymosin alpha$_1$.

4. The method of claim 1 wherein the thymosin is thymosin fraction 5.

5. The method of claim 1 wherein the thymosin is thymosin fraction 5 and the dosage is between about 60 and 120 mg per square meter of body area of the human twice weekly subcutaneously.

6. The method of claim 1 wherein the hepatitis is chronic.

7. The method of claim 1 wherein the thymosin is thymosin alpha$_1$, which has been chemically synthesized.

8. The method of claim 1 wherein mononuclear blood cells of the patient in vitro produce gamma interferon levels which are above those produced by mononuclear blood cells from a human without the hepatitis B.

9. A method for the treatment of a viral hepatitis patient having hepatic decompensation as defined as cirrhosis of the liver that results in hepatic failure and for increasing total lymphocyte, CD3 and CD4 counts in a human patient having low total lymphocyte, CD3 and CD4 counts compared to the levels in persons without the hepatitis which comprises:

(a) administering by injection subcutaneously an effective dosage of a thymosin selected from the group consisting of thymosin alpha$_1$ and a bovine calf extract containing thymosin alpha$_1$ in an effective amount so as to render said patient seronegative for the hepatitis viral DNA; and (b) regularly testing the patient to determine that there is an increase in absolute lymphocyte, CD3 and CD4 counts above those for persons without hepatitis during the administration, over the period of the administration of the thymosin to determine if the administration of the thymosin is effective.

10. The method of claim 9 wherein the thymosin is thymosin alpha$_1$ and the dosage is between about 600 and 1200 micrograms per square meter of body area of the human twice weekly subcutaneously.

11. The method of claim 9 wherein the thymosin is thymosin fraction 5 and the dosage is between about 60 and 120 mg per square meter of body area of the human twice weekly subcutaneously.

12. The method of claim 9 wherein the hepatitis is hepatitis B and mononuclear blood cells of the patient in vitro produce gamma interferon levels which are above those produced by mononuclear blood cells from a human without the hepatitis B.

13. The method of claim 9 wherein the virus is hepatitis B virus.

14. The method of claim 2 wherein the thymosin is thymosin alpha 1 and the dosage is between about 600 and 1200 micrograms per square meter of body area of the human administered twice weekly subcutaneously.

* * * * *